United States Patent
Banuchi

[11] Patent Number: 6,029,271
[45] Date of Patent: Feb. 29, 2000

[54] FACIAL SUN BLOCK MASK

[76] Inventor: Isabel M. Banuchi, Avenida Domenich 302, Hato Rey, Puerto Rico 00918

[21] Appl. No.: 09/044,849

[22] Filed: Mar. 20, 1998

Related U.S. Application Data

[60] Provisional application No. 60/042,053, Mar. 20, 1997.

[51] Int. Cl.⁷ ..................................................... A61F 9/02
[52] U.S. Cl. ................................. 2/9; 2/432; 2/435; 2/12
[58] Field of Search ............................ 2/6.3, 15, 12, 13, 2/426, 427, 432, 436, 435, 9, 10

[56] References Cited

U.S. PATENT DOCUMENTS

| | | | |
|---|---|---|---|
| Re. 32,638 | 4/1988 | Nesler | 2/436 |
| 4,309,775 | 1/1982 | Jory | 2/12 |
| 4,425,669 | 1/1984 | Grendol et al. | 2/436 |
| 4,447,914 | 5/1984 | Jannard | 2/432 |
| 4,556,995 | 12/1985 | Yamamoto | 2/439 |
| 4,701,965 | 10/1987 | Landis | 2/428 |
| 4,989,274 | 2/1991 | Patelski | 2/436 |
| 5,363,512 | 11/1994 | Grabos, Jr. et al. | 2/436 |
| 5,647,060 | 7/1997 | Lee | 2/9 |
| 5,756,010 | 5/1998 | Appel et al. | 252/589 |
| 5,765,223 | 6/1998 | McCausland | 2/9 |

OTHER PUBLICATIONS

Banucci Sun Block Mask Prevents UV Exposure Without Chemicals, Medco Forum, vol. 5 No. 2, Feb. 1998.

*Primary Examiner*—John J. Calvert
*Assistant Examiner*—Tejash D Patel
*Attorney, Agent, or Firm*—Parkhurst & Wendel, L.L.P.

[57] ABSTRACT

A facial sun block mask having a lens that is resistant to ultraviolet radiation. The lens is formed to protect most, if not all, of the face of the wearer. The lens is attached to a main body or visor that seat firmly against the upper forehead region of the wearer. The main body may also have vents.

4 Claims, 6 Drawing Sheets

FACIAL SUN BLOCK MASK

REFERENCE TO RELATED APPLICATION

This application claims benefit of provisional application Ser. No. 60/042,053 filed Mar. 20, 1997.

BACKGROUND OF THE INVENTION

In recent years, society has become more informed of the harmful effects to the skin, especially the face, of ultraviolet (UV) radiation. A variety of ways have been proposed (and used) to deal with UV radiation. Sunscreen lotions and sun block lotions having high and very high sunscreen performance factors (SPFs) are now very popular. Treated sunglasses to block UV radiation are also in abundance. Lotions have a tendency to rub and wear off and sunglasses give little protection to the face itself.

The present invention is another weapon in the war against the harmful effects of ultraviolet radiation.

DESCRIPTION OF THE INVENTION

The present invention is directed to a new device that is an alternative to conventional sun block lotions for protecting the skin (and particularly the face) against the damaging rays of the sun. The device, a sun block mask, is designed to protect the face in a physical manner against the sun's rays. The components of the mask are made of plastic materials, the lens thereof being formed of a high quality optic lens that is treated with an ultraviolet coating. Alternatively, the lens may be made of a material that itself provides blocking of ultraviolet rays from the sun. Preferably, the sun block mask physically blocks ultraviolet radiation below 380 nm. The mask helps prevent photoaging and is highly recommended for people with sun-induced diseases and to prevent skin cancer.

DETAILED DESCRIPTION OF THE DRAWINGS

Figure 1:
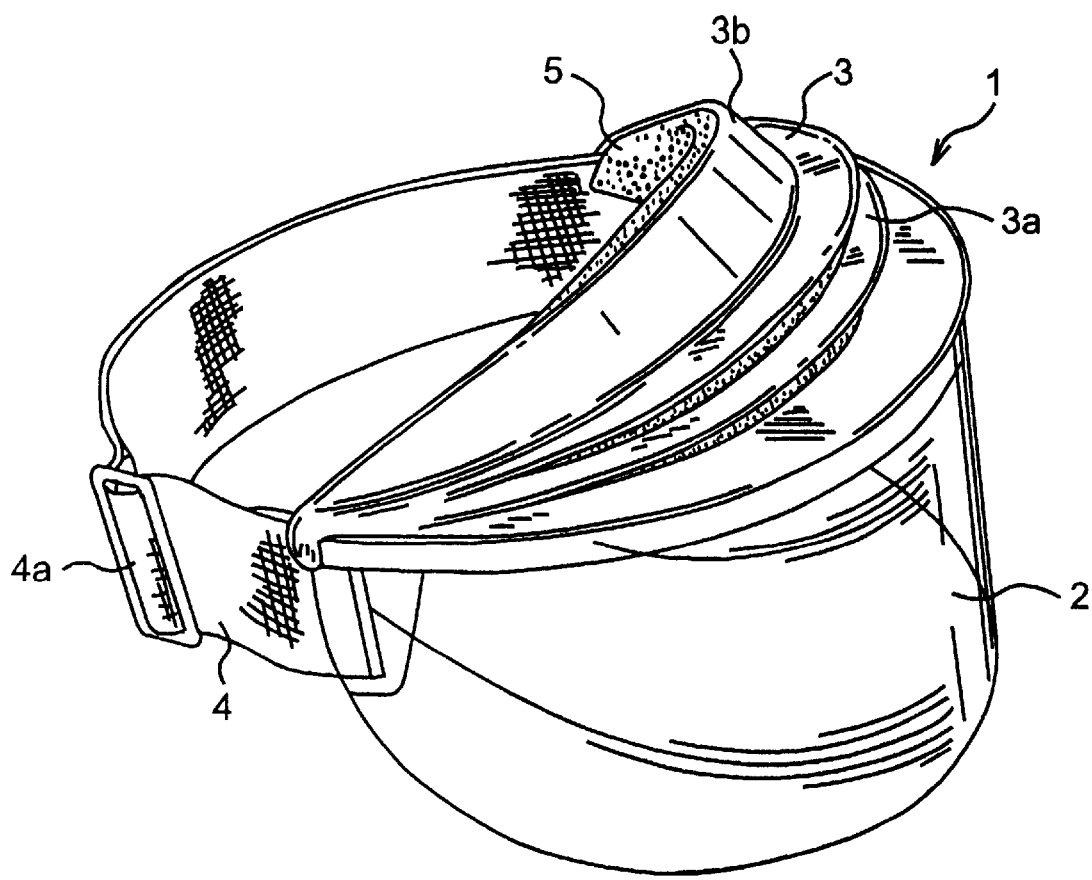
FIG. 1 is a perspective view of one embodiment of the facial sun block mask of the present invention.
Figure 2:
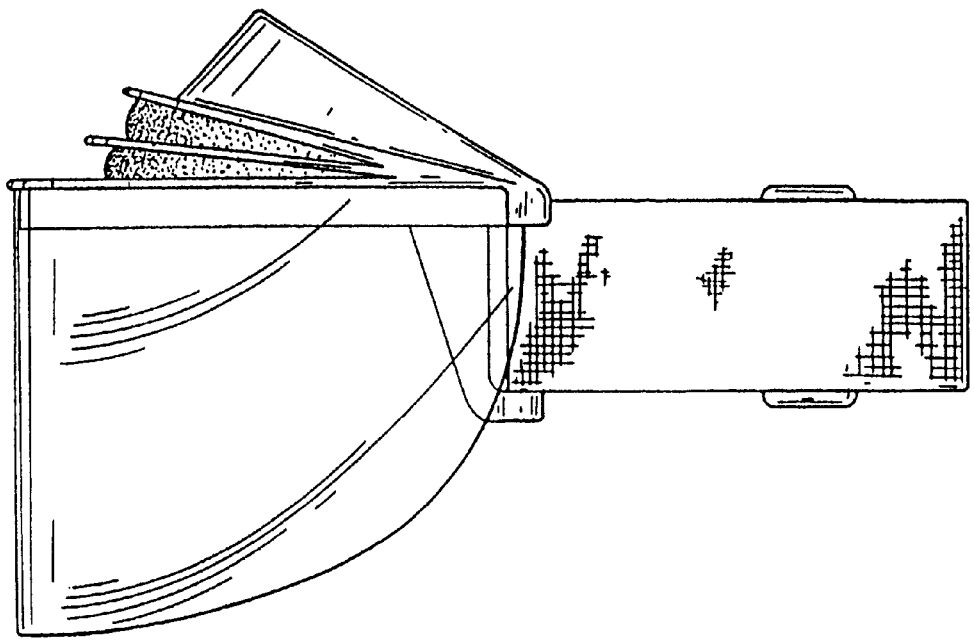
FIG. 2 is a left side view of the mask of FIG. 1.
Figure 3:
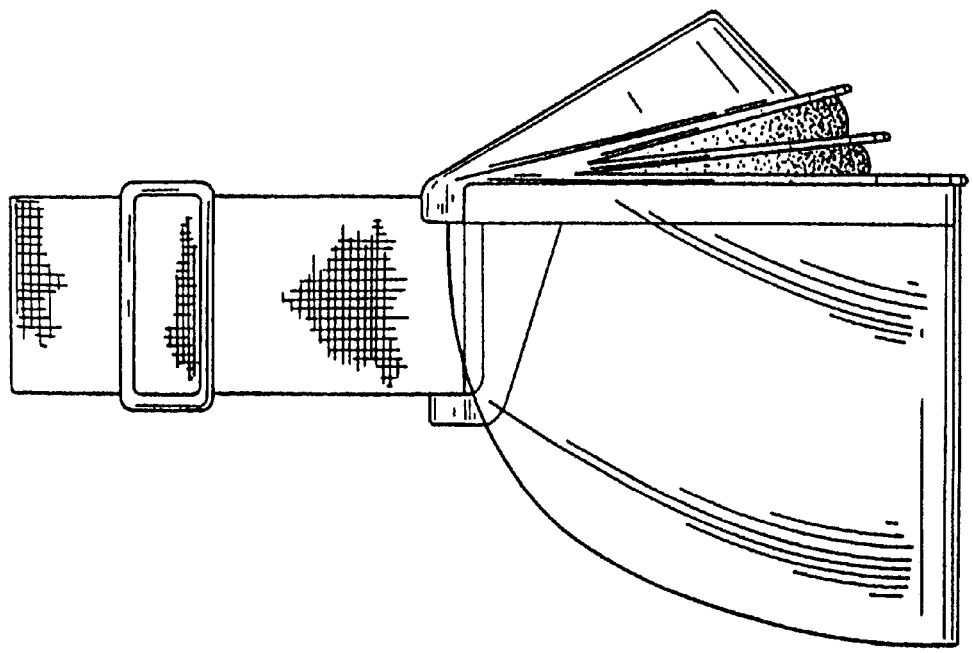
FIG. 3 is a right side view of the mask of FIG. 1.
Figure 4:
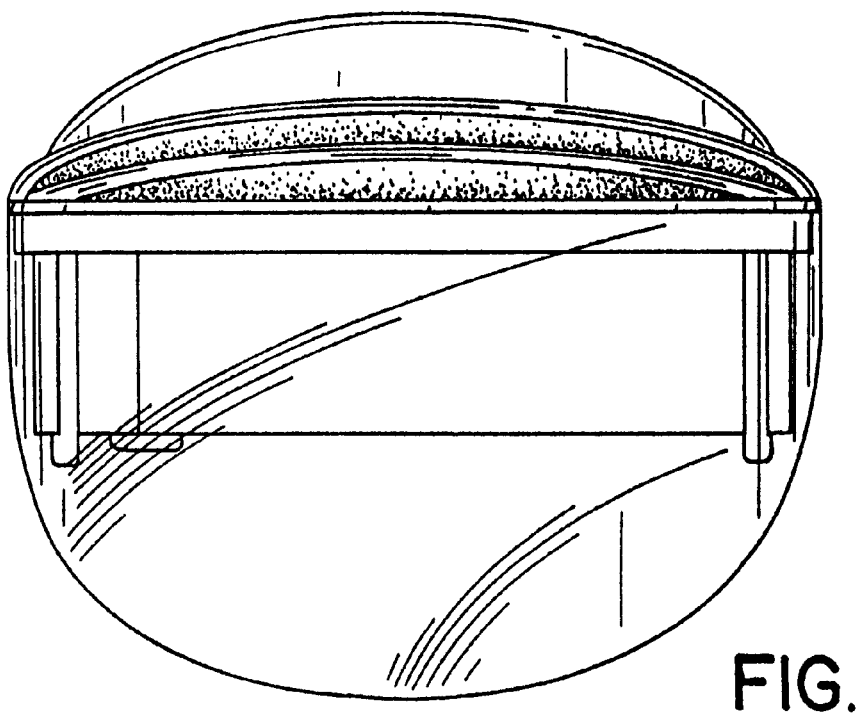
FIG. 4 is a front view of the mask of FIG. 1.
Figure 5:
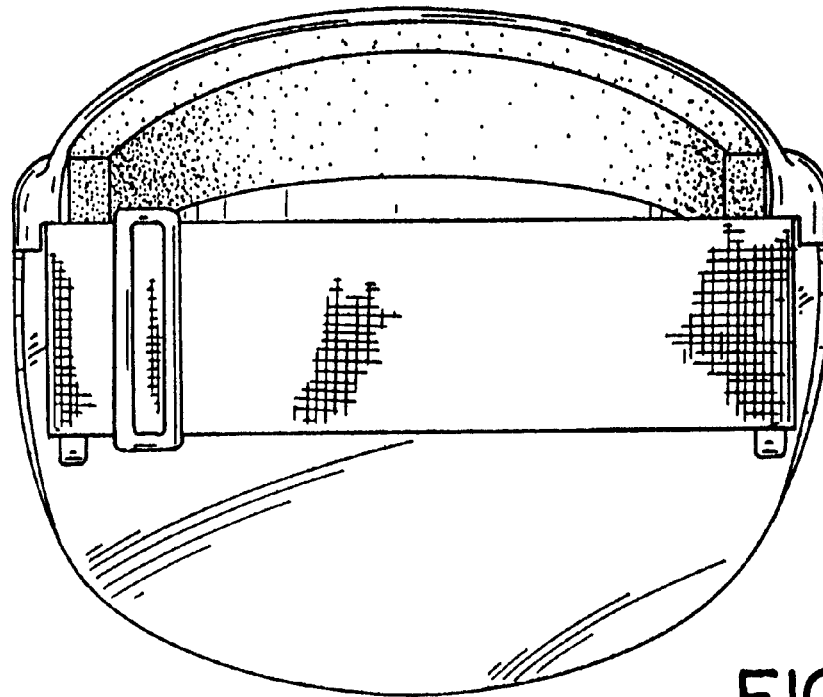
FIG. 5 is a back view of the mask of FIG. 1.
Figure 6:
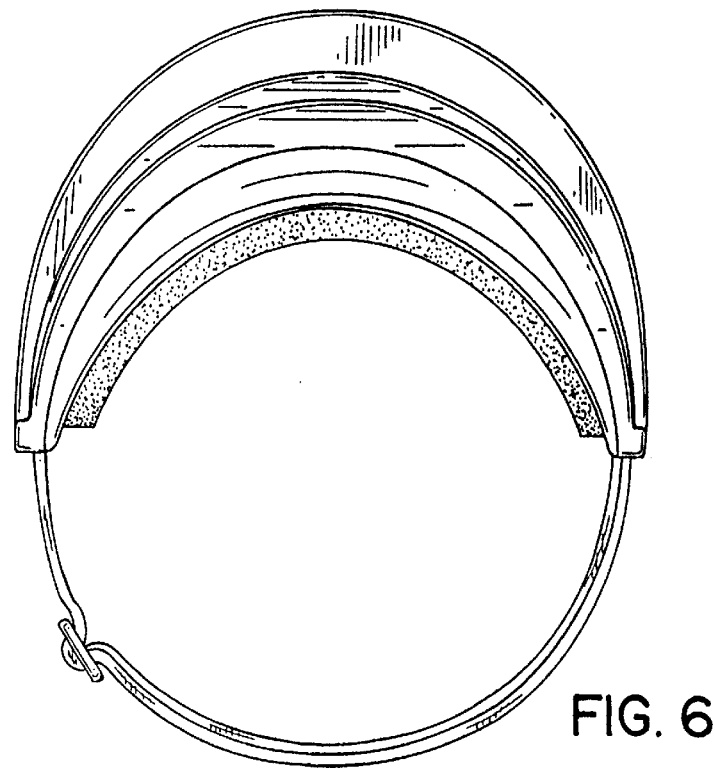
FIG. 6 is a top view of the mask of FIG. 1.
Figure 7:
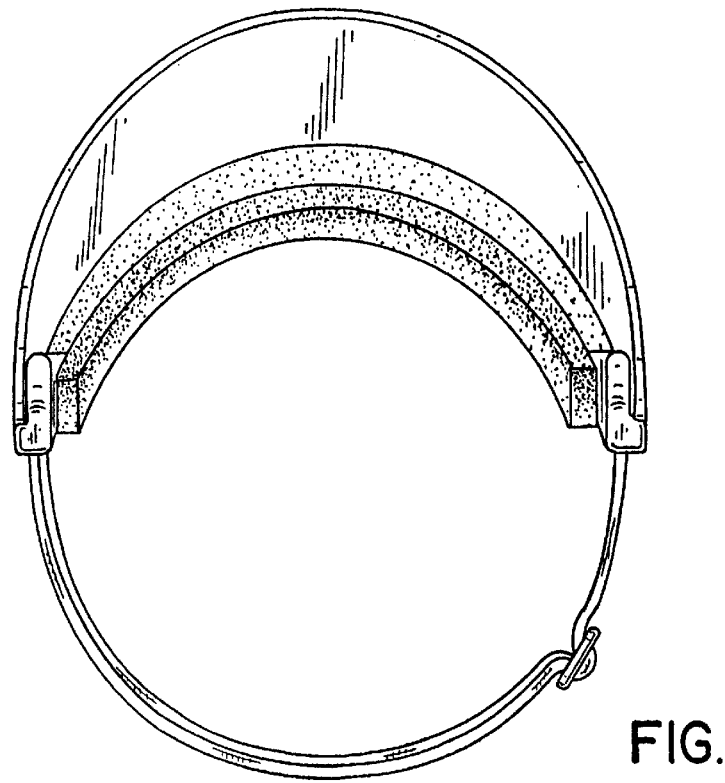
FIG. 7 is a bottom view of the mask of FIG. 1.

Referring to the drawings, FIGS. 1–7 illustrate several views of a first embodiment of a facial sun block mask of the invention. As shown, sun block mask 1 includes lens 2 that is adapted to block harmful UV rays. Lens 2 extends from main body 3, having a plurality of vents 3a therein for increased comfort, to allow heat and perspiration to pass therethrough. Main body 3 also includes an arcuate-shaped seating portion 3b that is adapted to seat firmly against the upper forehead region (slightly above the hairline, for example) of the wearer for a secure fit. Foam liner 5 lines seating portion 3b for wearing comfort, and is provided within vents 3a to prevent passage of harmful UV rays through the vents 3a. The mask 1 is secured to the head of the wearer via elastic strap 4 that is adjustable via buckle 4a.

Lens 2 can be formed of any one of known high quality optic materials, including lightweight plastics commonly found in high quality, high performance eyewear for sport applications. Main body 3 is preferably formed of a lightweight opaque plastic material that resists degradation due to exposure to UV rays over time. The particular materials for foam 5 liner and the elastic strap 4 may also be chosen by one of ordinary skill in the art, as desired.

Figure 8:
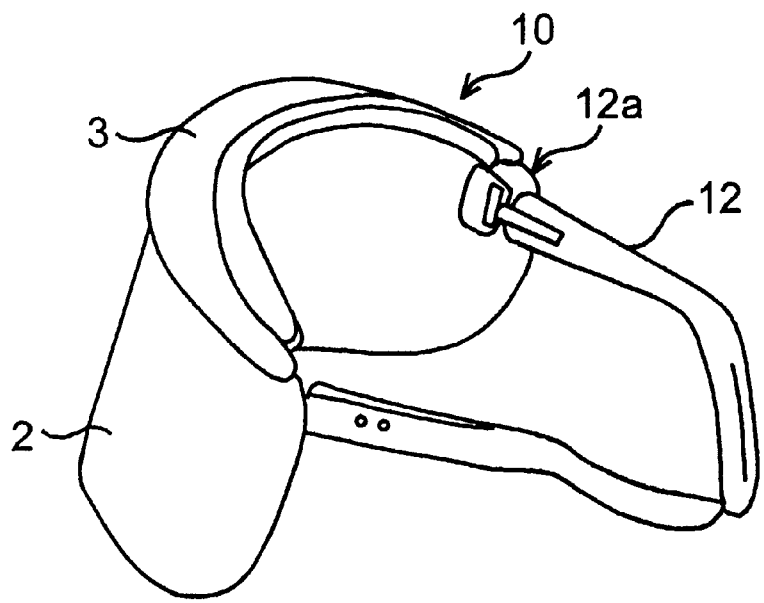
FIG. 8 is a perspective view of a second embodiment of the facial sun block mask of the present invention.
Figure 9:
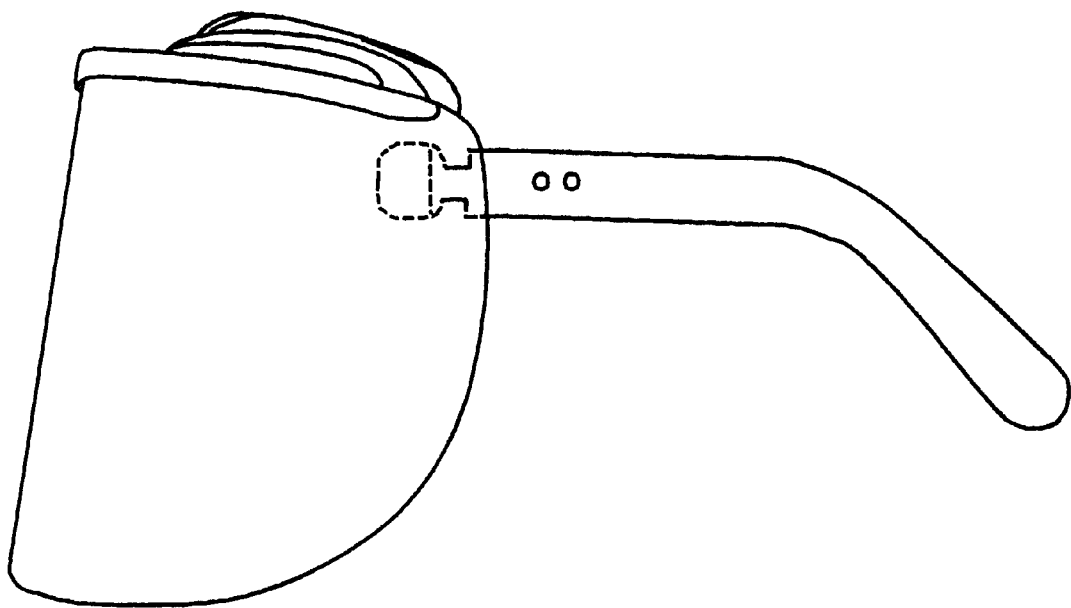
FIG. 9 is a side view of the mask of FIG. 8.

FIGS. 8 and 9 depict a second embodiment of the facial sun block mask according to the present invention. Mask 10 includes the lens 2 and main body 3 formed in a similar fashion to the first embodiment discussed above. However, mask 10 includes temples 12 hinged to lens 2 via hinges 12a, rather than elastic strap 4 as in the first embodiment. According to the second embodiment of the invention, the advantageous sun blocking effects of the first embodiment are maintained, but temples 12 provide an alternative means for securing the mask to the head of the wearer. The temples 12 advantageously provide ease of donning and removal from the face of the wearer.

Figure 10:
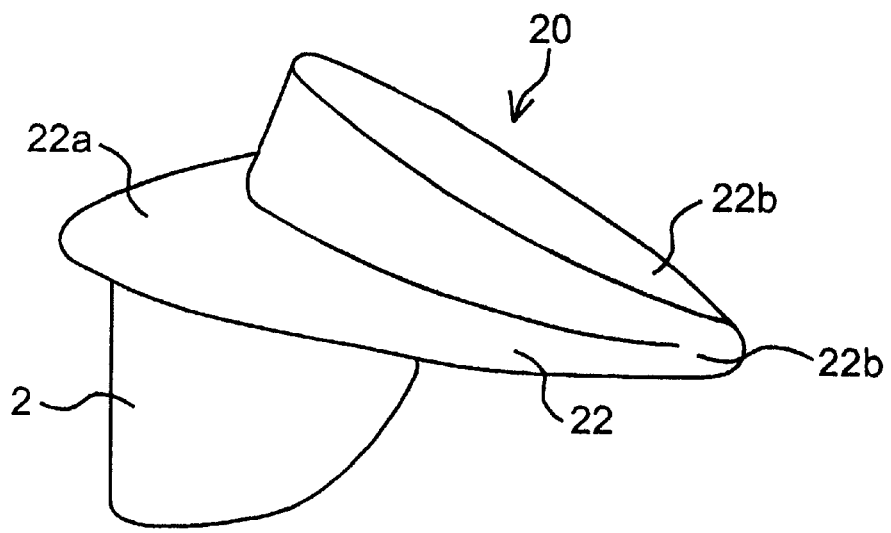
FIG. 10 is a perspective view of a third embodiment of the facial sun block mask of the present invention.
Figure 11:
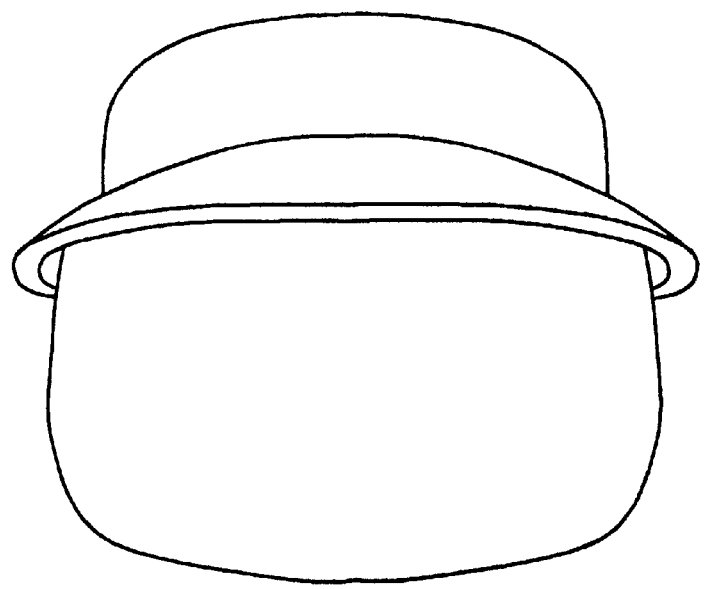
FIG. 11 is a front view of the mask of FIG. 10.

FIGS. 10 and 11 show a third embodiment of the present sun block mask. Mask 20 includes lens 2 as in the first embodiment. However, here, lens 2 is secured to sun visor cap 22 having visor 22a. Sun visor cap 22 is secured to the head of the wearer via a clip-type structure. Particularly, sun visor 22 terminates at ends 22b that can be elastically deformed for donning by the wearer, and which press against lateral portions of the head of the wearer, above the ear lobes, to provide a secure fit. The third embodiment provides yet another alternative for preventing sun damage to the face of the wearer. Although not shown in FIGS. 10 and 11, visor 22a may also include vents as in the first and second embodiments. Additionally, the sun visor cap can be formed integrally of an injection-molded plastic material, as generally known in the art.

The present invention as illustrated in the above drawings provides a particularly unique article that can provide a great benefit in minimizing sun damage to the skin, an ever-increasing worldwide problem. The present invention offers complete UV protection for the facial area, can be used with or without sunscreens, and provides an effective alternative for patients allergic to sunscreens. The invention provides particularly unique applications for patients after cosmetic procedures including laser skin resurfacing, dermabrasion, chemical peels, face lifts and Blepharoplasty. The present invention prevents, reduces and helps counteract sun-induced diseases such as Melasma or Lupus.

What is claimed is:

1. A facial sun block mask comprising:
    a main body for placement on the forehead of a wearer, said main body having an arcuate-shaped seating portion adapted to seat firmly against the upper forehead of the wearer;
    a lens attached to said main body, said lens constructed of a material that blocks ultraviolet radiation, said lens having a higher-most portion; and an adjustable elastic strap attached to said main body;

wherein said main body includes a lower-most portion for attachment to said lens, the higher-most portion of said lens not extending beyond said lower-most portion of said main body, said main body also including a plurality of vertical vents located opposite the higher-most portion of the lens with respect to said lower-most portion of said main body.

2. The facial sun block mask of claim 1, wherein said lens is an optic lens having a coating to block ultraviolet radiation.

3. The facial sun block mask of claim 1, wherein said lens is made of an ultraviolet radiation-blocking material.

4. The facial sun block mask of claim 1, wherein said main body has attached thereto a foam liner.

\* \* \* \* \*